(12) United States Patent
Hofmann

(10) Patent No.: US 6,811,688 B1
(45) Date of Patent: Nov. 2, 2004

(54) CHROMATOGRAPHY COLUMNS

(75) Inventor: Martin John Hofmann, Stroud (GB)

(73) Assignee: Downstream Media Limited, Gloucestershire (GB)

( * ) Notice: Subject to any disclaimer, the term of this patent is extended or adjusted under 35 U.S.C. 154(b) by 0 days.

(21) Appl. No.: 09/979,576

(22) PCT Filed: May 19, 2000

(86) PCT No.: PCT/GB00/01937

§ 371 (c)(1),
(2), (4) Date: Feb. 15, 2000

(87) PCT Pub. No.: WO00/72002

PCT Pub. Date: Nov. 30, 2000

(30) Foreign Application Priority Data

May 20, 2000 (GB) .............................................. 9911797

(51) Int. Cl.[7] .............................................. B01D 15/08
(52) U.S. Cl. ........................ 210/198.2; 210/656; 96/101
(58) Field of Search ................................. 210/635, 656, 210/659, 198.2; 96/101

(56) References Cited

U.S. PATENT DOCUMENTS

| | | | | |
|---|---|---|---|---|
| 3,826,373 A | * | 7/1974 | Andreotti ................. | 210/198.2 |
| 4,289,620 A | | 9/1981 | Hara ....................... | 210/198.2 |
| 4,510,058 A | | 4/1985 | Cais et al. ................. | 210/657 |
| 4,888,112 A | * | 12/1989 | Kronwald ................ | 210/198.2 |
| 5,194,225 A | | 3/1993 | Muller et al. ................. | 422/70 |
| 5,266,193 A | | 11/1993 | Kimura et al. ........... | 210/198.2 |

FOREIGN PATENT DOCUMENTS

| | | | | |
|---|---|---|---|---|
| EP | 0 476 997 | | 3/1992 | .............. 210/198.2 |

OTHER PUBLICATIONS

Patent Abstracts of Japan, vol. 015. No. 462 (P–1279), Nov. 22, 1991, & JP 03 197863 A ( Iosoh Corp 129 Aug. 1991, abstract.

* cited by examiner

*Primary Examiner*—Ernest G. Therkorn
(74) *Attorney, Agent, or Firm*—Pearne & Gordon LLP

(57) ABSTRACT

A chromatography column suitable for small-scale laboratory use as a column tube resembling that of a syringe and a movable plunger which slides in the column tube. End filter arrangements are mounted by direct integration, e.g. melt-bonding of glass, into these components. A tubular stem providing an internal flow conduit to the end filter arrangement at the front end of the plunger is also integrally bonded behind the permeable filter portion. By making all of these operational components out of a formable, melt-bondable material, preferably glass which can also make sliding seals with itself, the resulting chromatography column is simple to use and unlikely to leak by comparison with conventional laboratory columns which use many discrete components.

23 Claims, 2 Drawing Sheets

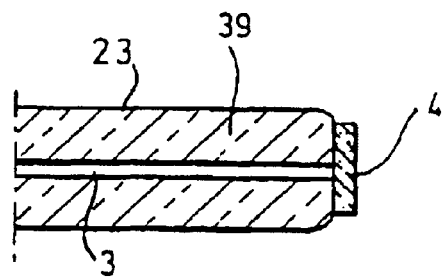
FIG.2
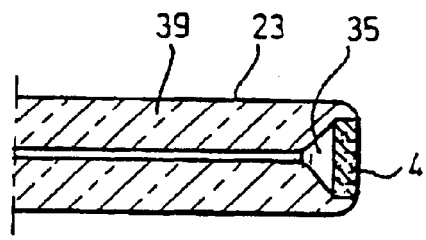
FIG.3
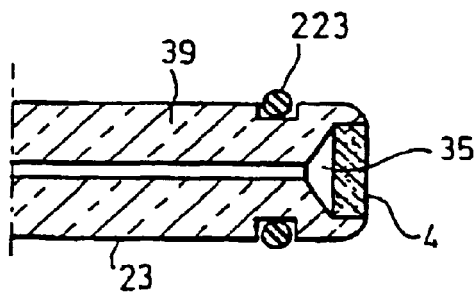
FIG.4
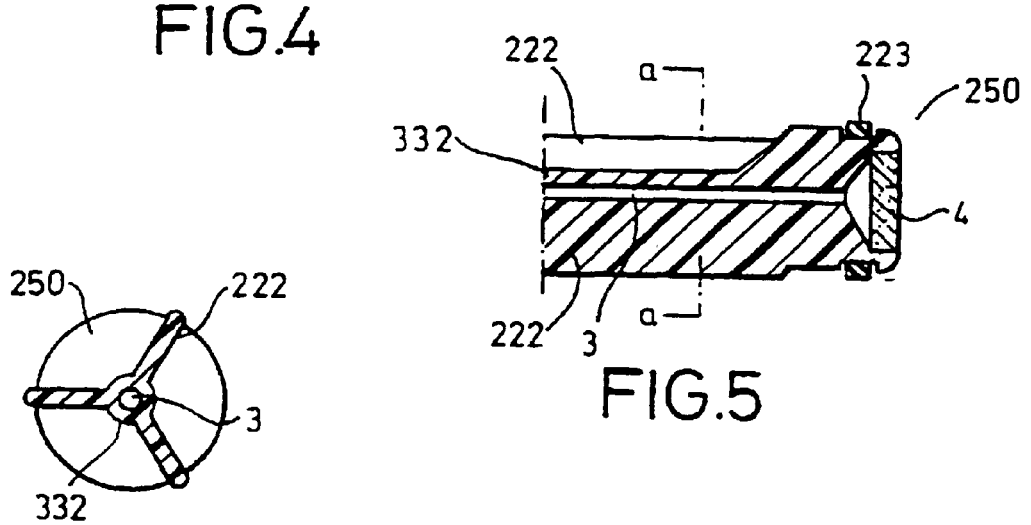
FIG.5
FIG.5a

CHROMATOGRAPHY COLUMNS

REFERENCE TO RELATED APPLICATIONS

This application is a 371 of PCT/GB00/01937 filed May 19, 2000.

FIELD OF THE INVENTION

This invention has to do with chromatography columns and in particular laboratory columns, i.e. small columns such as are used for bench scale or research work.

BACKGROUND OF THE INVENTION

Generally speaking a column of the relevant kind (referred to herein as being "of the kind described") has a column tube and end filter arrangements which, in use, retain a bed of particulate chromatography medium in the column tube between them while allowing the passage of fluid for chromatography. At least one of the end filter arrangements is at the front end of a plunger which is axially slidable along inside the tubular column, makes a seal outwardly against the column tube and incorporates an internal flow conduit communicating along the plunger between a filter portion of the filter arrangement and a rear part of the plunger outside the column tube.

PRIOR ART

Columns of the kind described are currently available at varying levels of cost and complexity.

The column tube is usually glass.

In sophisticated versions the plunger shaft has outer and inner concentric plastic tubes. The inner tube may be a thick solid tube, with a narrow bore providing the flow conduit. Or it may be a wide-bored tube housing an inmost flexible tube which is the flow conduit. At the front end of the shaft a rubber sealing ring is trapped between end formations of the inner and outer stiff tubes, and the filter arrangement has a porous disk (e.g. a sinter or mesh) clamped over a divergent flow distributing end surface of the inner tube, at the outlet of the flow conduit. The outer stiff tube runs slidably through a plastics end unit screwed onto the end of the column tube. The end unit has a mechanism which may be switched between a free sliding engagement with the plunger's outer plastics tube (for large axial movements) and a screw-threaded engagement (for fine adjustments). An internal screw engagement is also provided between the inner and outer tubes so that after advancing the plunger to the desired position—i.e. contacting the end of the bed of medium—the rubber sealing ring can be squeezed out into sealing contact with the column tube wall by axially compressing it between the end formations of the inner and outer tubes. Internal plunger seals are also provided to prevent leakage from between the internal conduit and the filter element into the interior of the plunger construction, or to the outside of the shaft. These columns give good results but can be very expensive, and are complicated to use and maintain.

Laboratory columns of another, simpler kind use short removable plugs at both ends of the column. The plugs are solid polymeric units having an outer O-ring seal to seal against the glass column wall, a narrow central bore for the fluid flow and a flat annular recess at the inner face which receives the porous filter disc. The plug has a very short travel into the column tube, so the media bed must be carefully filled to the correct depth. The necessarily tight-fitting seal makes it hard work to push the plug into the column end. The outside of the glass tube end is threaded to take a clamping nut which holds the plug in once installed. These columns are simpler and cheaper than known plunger columns of the kind described, but less versatile.

SUMMARY OF THE INVENTION

A first proposal herein is that the plunger of a column of the kind described comprises a tubular stem of glass or other formable material, preferably transparent, which defines in one piece the internal fluid flow conduit. The permeable filter element is integrally bonded to the front end of this tubular stem across the internal fluid flow conduit.

In particular the filter element is preferably bonded to the plunger stem by being integrally fused therewith, e.g. by heat-fusing. The materials of the filter element and stem can be selected for compatibility in this respect, e.g. both may be of glass or a suitable thermoplastics material. A preferred version has a glass stem fused to a sintered glass filter element.

Preferably the tubular stem defining the internal fluid flow conduit extends as a one-piece integral whole rearwardly to a rear connection union at the rear of the plunger, i.e. a threaded union, spigot or ferrule. Preferably this union has a joint boundary which is exterior of the plunger stem. Like the integral bonding of the filter element at the front end, this one-piece construction provides a simple means for preventing leakage within the plunger which is a significant difficulty with prior art constructions.

A further proposal, preferably combined with the above, is that a one-piece integral construction joins the permeable filter element and an outwardly-directed sealing portion at or adjacent the front end of the plunger which makes a seal directly against the column tube wall, or which mounts a deformable seal element for making such a seal.

In particular the filter element is preferably bonded to the plunger's outer wall by being integrally fused therewith, e.g by heat-fusing. Again, use of glass or thermoplastics material for the filter element and plunger outer wall is advantageous in this respect; a sintered glass filter element may be fused to an outer glass wall of the plunger.

A further independent proposal herein, again preferably combined with the above, is that the plunger comprises a tubular stem of glass or other formable material which defines, preferably in one piece, the internal fluid flow conduit, and also an outer plunger wall spaced outwardly from the tubular stem, the outer plunger wall and tubular stem being integrally bonded to one another at the front end of the plunger so as to seal off the internal space of the plunger at the front end. Preferably one or both of the stem and plunger outer wall is/are integrally bonded to the filter element, as in the first and/or second aspects set out above. Again the use of fused glass or other thermoplastics is advantageous. Prevention of leakage to within the plunger structure can therefore be prevented reliably without additional internal sealing components. By combination with the other aspects above, the entire internal fluid flow path from a rear connection union to the permeable filter element can be sealed vis à vis the plunger interior without requiring seal components between discrete mechanical parts. The use of glass or other suitable thermoplastics enables such a construction to be made easily e.g using conventional plastics-forming or glass-blowing techniques. Furthermore the use of a transparent material enables the user to observe the flow of material within the plunger.

An outwardly-directed sealing portion at or adjacent the front end of the plunger may have a plunger wall surface which is shaped e.g by machining or moulding, most preferably a machined glass surface, to fit and seal directly against the column tube wall. The use of ground glass surfaces to make fluid-tight seals is as such well-known in the laboratory context. The present proposal can exploit this in a new way, enabling a special advantage in combination with the other aspects as described above and the transparency available with glass material. Machined glass surfaces are not highly transparent but become so when in wetted contact with another glass surface. The plunger exterior may thus have a cylindrical sealing portion making a fitting seal against the column tube wall interior. This sealing portion may be axially elongate, so as to align the plunger axially in the column and avoid the need for column tube end units as were required in the prior art. The same advantage may be achieved by other plunger constructions providing an axially-elongate fitting engagement inside the column tube, e.g axially-extending fins or the like behind the sealing portion which may itself then be shorter.

The plunger may be made with a deformable e.g resilient sealing element such as a sealing ring, preferably an O-ring seal, fitting around the plunger's outer wall to make a sealing arrangement against the column tube wall.

The internal fluid flow conduit preferably has an elongate portion of relatively narrow cross section (e.g less than 1 or 2 mm diameter) and a divergent (larger cross-section) distribution portion immediately adjacent to the permeable filter element. Where the internal tubular conduit is provided in a discrete tubular stem within an outer plunger wall, the tubular stem is preferably flared at its lower end to provide this divergence. Again this is easy to do with glass or thermoplastics tubular stems.

Particularly in smaller size columns, the plunger may be essentially a solid rod whose outer surface opposes the column wall, with a narrow central bore for the fluid flow conduit. In this case the front end of the rod may be shaped to form a divergent zone around the front opening of the flow bore.

The plunger can resemble that of a syringe. It may have a head at its rear (outward) end adapted for manual pushing. Preferably a rear connection union for the internal fluid flow conduit emerges transversely from the plunger, below such a head.

The column tube wall may be double-ended as in known constructions, and plungers as described above may be deployed at both ends. More preferably however we propose that one end of the column tube wall has a full-diameter opening receiving the mentioned plunger and the other end is a closed end, converging to a union for an external fluid flow conduit, with a fixed permeable filter element across the column tube adjacent the closed end. The fixed permeable element may be permanently installed, e.g a glass sinter disc fused into a glass column tube wall. Or, a mount may be provided for fixed mounting of an exchangeable filter element.

The volume of the column is typically not more than 100 ml.

BRIEF DESCRIPTION OF THE DRAWINGS

Embodiments of the invention are described with reference to the accompanying drawings, in which FIGS. 2–5 and 5A illustrate some possible variants of plunger construction.

DETAILED DESCRIPTION OF PREFERRED EMBODIMENTS

Figure 1:
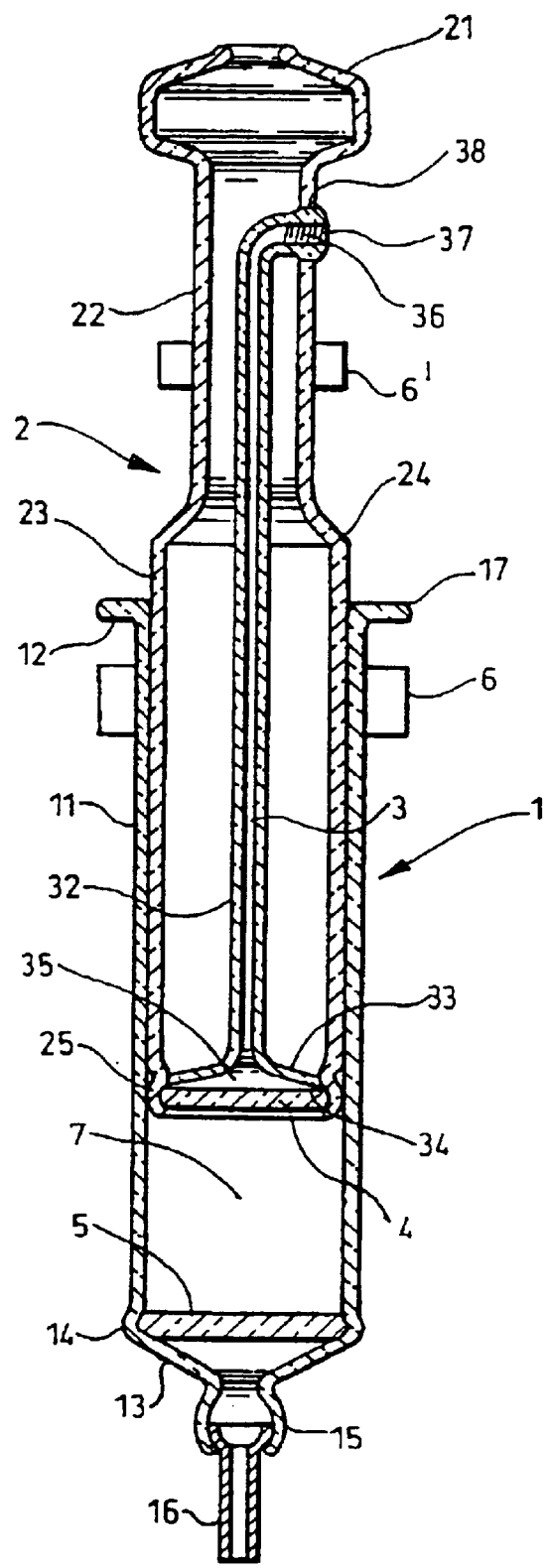
FIG. 1 is an axial cross-sectional view of a laboratory chromatography column embodying the invention.

With reference to FIG. 1, an all-glass laboratory chromatography column consists of a column tube 1 in which a plunger 2 fits slidably The column tube 1 in this embodiment is the tube of a commercially-available syringe. Its volume is for example 50 ml. At its upper open end it has a conventional flange 12 with a flat 17 at one side to prevent rolling The column has the usual uniform cylindrical wall 11, which can conveniently be mounted upright in a laboratory clamp 6. The lower end of the column has an integral convergence 13 to a nozzle 15, in which a metal spigot 16 is incorporated to form an outlet union connectable, e.g by a conventional ferrule, to an outlet pipe if desired.

A sintered glass filter disc 5 is fixedly mounted across the lower end of the tube 1 at the transition to the convergent portion 13. The tube wall at this portion 14 has been heat deformed and fused with the periphery of the glass sintered disc 5 to form a permanent joint.

The glass column wall 11 is transparent in the usual way.

The plunger 2 is also an all-glass construction, made from standard laboratory glass using standard glass-forming techniques. Its three main components are a central tubular stem 32 defining a flow conduit 3, an outer tubular housing wall 22 surrounding the stem and having a top head 21, and a sintered glass permeable filter disc 4 mounted in the front end of the stem.

The tubular outer wall 22 has a lower portion extending approximately half the length of the plunger, nearly to the front end, which has a machined glass surface 23 making a sliding sealing fit against the inner surface of the column tube wall 11. By this means the plunger 2 defines with the column tube 1 a sealed internal bed space 7 between the upper and lower filter elements 4,5. No resilient seal element is required, although one may be used if desired adjacent to the front end. The elongate close-fitting glass surface 23 also maintains axial alignment of the plunger 2 in the column 1. Above a shoulder 24 at the top of the machined surface 23 the plunger 22 narrows, so that it can be slid as far down as desired inside the column tube 1. A chromatography medium bed of any desired length can therefore be established in the space 7. A laboratory clamp 6' suffices to hold the plunger down in contact on top of the medium bed.

The internal tubular stem 32 of the plunger can be made from stock glass tubing e.g of 1 mm bore. Using standard glass forming techniques its lower end is flared outwardly to form a divergent section 33 and its periphery is fused onto the upper surface of the glass sinter disc 4. A fused joint is also established between the mouth 25 of the outer glass wall 22 and the periphery of the sinter disc 4, and onto the edge of the divergent portion 33 of the central stem. By exploiting glass' intrinsic propensity for forming and fusing by simple hot manipulations, this provides a plunger end construction which is fully internally sealed (i.e preventing leaks into the space between the stem 32 and outer wall 22) and externally sealed against the column wall 11, without requiring any discrete sealing elements. It is also fully transparent, so that the user can observe the flow of sample through the conduit 3 and down onto the sinter disc 4, verifying the absence of trapped air in the divergent space 35 above the disc 4—this latter is important, and difficult to check in conventional opaque constructions.

It is generally desirable to minimize the volume of the distribution space 35 and not difficult to do so in thermoformable material. The same applies to the lower convergence 13 of the column tube.

The surface groove around the outer wall behind the joint to the disc will provide a useful seating for a discrete deformable seal element, either additionally to the glass-glass seal illustrated or, in an alternative embodiment, as the sole external seal.

At its upper end the central tubular stem 32 is bent sideways and emerges through the outer tubular wall 22, below the enlarged head 21. The end of the tube 32 is bonded into this opening by a thermally-fused joint 38, completing the sealing of the fluid flow path in the plunger vis á vis the exterior. The upper opening of the tube mouth 37 has a connection union formed with an internal glass thread 36. Alternatively, the tube may project laterally beyond the column wall 22 as a nozzle to house a metal spigot of the kind used at the bottom of the column 1, or some other suitable union may be used.

It will be noted that the head 21 is clear of the union opening 37 so that the plunger can be manipulated without interfering with the fluid connection.

The skilled reader will appreciate that the various integrally-fused bonds created in this embodiment, exploiting the properties of glass, individually provide advantages over prior art constructions. Useful embodiments of our proposals can therefore be made with only some of these integral bonds, and/or using different materials. The double-tube construction shown in FIG. 1 may be too elaborate for very small columns, and FIG. 2 shows the end of a plunger for a small column, in which a single hollow glass rod provides both the exterior surface 23 and the internal conduit 3 of the plunger. In this very simple structure the divergence at the front end of the conduit is dispensed with and the sinter disc 4 is fused or otherwise bonded directly onto the front face of the tubular rod 39.

FIG. 3 shows a similar solid-rod construction, modified by the machining of a divergent chamber 35 immediately upstream of the permeable disc 4, and the recessing of the disc 4 into the front face of the rod 39.

In the FIG. 2 and FIG. 3 constructions the outer surface 23 of the rod effects the seal against the tube wall. FIG. 4 shows how additionally or alternatively a deformable seal element such as a rubber O-ring 223 or a PTFE ring may be fitted around the front end of the plunger exterior.

In all of the above embodiments a full cylindrical contact of the plunger in the column tube assures the axial alignment of the two main components. However this is not essential, and particularly in plastics constructions material may be saved by using a construction as in FIG. 5. Here a one-piece moulded plastics entity forming the plunger has a central tubular portion 332 defining the internal conduit 3, surrounded by axially-extending fins 222 which provide the necessary axial alignment against the column tube wall, and a solid end unit 250 providing the necessary seal against the tube wall, e.g via PTFE ring 223, and the surrounding fused or bonded join to the permeable filter element 4.

What is claimed is:

1. A chromatography column having a column tube and end filter arrangements which, in use, retain a bed of particulate chromatography medium in the column tube between them while allowing the passage of fluid for chromatography;
at least one of the end filter arrangements being at the front end of a plunger which is axially slidable along inside the column tube, makes a seal outwardly against the tube and incorporates an internal flow conduit communicating along the plunger between a permeable filter portion of the respective end filter arrangement and a rear part of the plunger outside the column tube;
the plunger comprising a tubular stem of glass or thermoplastic material which defines in one piece said internal flow conduit including an integral front divergent portion, the permeable filter portion being integrally bonded to the front end of the tubular stem across the front divergent portion of the internal flow conduit to form an internal distribution space, and an outer plunger wall spaced outwardly from said tubular stem at locations rearward of the front divergent portion of the internal flow conduit, the outer plunger wall and tubular stem being integrally bonded to one another around said tubular stem at the front divergent portion so as to seal off an internal space at the front end of the plunger.

2. A chromatography column according to claim 1 in which the filter portion is integrally fused to the plunger stem.

3. A chromatography column according to claim 2 in which both stem and filter portion are of glass or thermoplastics material.

4. A chromatography column according to claim 1 in which the tubular stem extends as a one-piece integral whole back to a rear connection union at the rear of the plunger.

5. A chromatography column according to claim 4 in which the rear connection union has a joint boundary at the exterior of the plunger stem.

6. A chromatography column according to claim 1 in which an outwardly-directed sealing portion at or adjacent the front end of the plunger which makes a seal directly against the column wall, or which mounts a deformable seal element for making such a seal, is joined to the permeable filter portion via a one-piece integral structure.

7. A chromatography column according to claim 6 in which the permeable filter portion is bonded to the plunger's outer wall by being integrally fused therewith.

8. A chromatography column according to claim 1 in which one end of the column tube has a full-diameter opening receiving the plunger and the other end is a closed end, converging to a union for an external fluid flow conduit and having a fixed permeable filter element across the column tube adjacent the closed end.

9. A chromatography column according to claim 1 in which the tubular stem and outer plunger wall are transparent.

10. A chromatography column having a column tube and end filter arrangements which, in use, retain a bed of particulate chromatography medium in the column tube between them while allowing the passage of fluid for chromatography;
at least one of the end filter arrangements being at the front end of a plunger which is axially slidable along inside the column tube, makes a seal outwardly against the tube and incorporates an internal flow conduit communicating along the plunger between a permeable filter portion of the respective end filter arrangement and a rear part of the plunger outside the column tube;
the plunger comprising a tubular glass stem which defines said internal flow conduit including an integral front divergent portion, the permeable filter portion being a sintered glass element integrally fused to the plunger stem around said tubular stem at the front divergent portion so as to seal off an internal distribution space at the front end of the plunger.

11. A chromatography column according to claim 10 in which the plunger further comprises an outer plunger wall spaced outwardly from said tubular stem at locations rearward of the divergent portion, the outer plunger wall and tubular stem being integrally bonded to one another at the front end of the plunger.

12. A chromatography column according to claim 11 in which the outer plunger wall has a cylindrical sealing portion whose outer surface makes a fitting seal against the column tube interior.

13. A chromatography column according to claim 12 in which the cylindrical sealing portion is axially elongate and constitutes the means for aligning the plunger axially in the column tube.

14. A chromatography column according to claim 12 in which the plunger comprises a sealing ring fitting around the outer plunger wall to seal against the column tube wall.

15. A chromatography column according to claim 11 in which the plunger comprises a sealing ring fitting around the outer plunger wall to seal against the column tube wall.

16. A chromatography column according to claim 10 in which one end of the column tube has a full-diameter opening receiving the plunger and the other end is a closed end, converging to a union for an external fluid flow conduit and having a fixed permeable filter element across the column tube adjacent the closed end.

17. A chromatography column according to claim 13 in which one end of the column tube has a full-diameter opening receiving the plunger and the other end is a closed end, converging to a union for an external fluid flow conduit and having a fixed permeable filter element across the column tube adjacent the closed end.

18. A chromatography column comprising a column tube and a self-aligning plunger axially slidably receivable in the column tube;

the column tube having a first end with a full-diameter opening closed by removably receiving the plunger and a second, closed end converging to a union for an external fluid flow conduit;

a fixed permeable filter element being provided across the column tube adjacent the second, closed end, to retain in use one end of a bed of particulate chromatography medium in the column tube while allowing the passage to said union of fluid for chromatography;

the plunger having a front end slidable inside the column tube and a rear end outside the column tube, the front end of the plunger comprising a further permeable filter element which retains in use the other end of a said bed of particulate chromatography medium in the column tube, and the rear end of the plunger having a rear fluid connection union;

the plunger comprising a tubular stem of glass or thermoplastic material which defines in one piece an internal flow conduit extending in the plunger from the rear fluid connection union to the permeable filter element, and having an integral front divergent portion across which the permeable filter element is disposed, the plunger further comprising an outwardly-directed sealing portion making a slidable seal engagement against the column tube wall, with an alignment structure of the plunger making an axially-elongate fitting engagement with the column tube wall to align the plunger axially in the column tube;

the plunger's permeable filter element being of glass or thermoplastic material and integrally bonded around so as to seal off an internal distribution space at the front end of the plunger.

19. A chromatography column according to claim 18 in which the column tube and plunger are transparent.

20. A chromatography column according to claim 18 in which the column tube and plunger are of glass.

21. A chromatography column according to claim 18 in which said alignment structure of the plunger is provided by an outer cylindrical plunger wall spaced outwardly from said tubular stem at locations rearward of the divergent portion, the outer plunger wall, tubular stem and permeable filter element being connected to one another by integral fusing of their glass or thermoplastic material to seal off an internal space of the plunger.

22. A chromatography column according to claim 18 in which the plunger has a machined glass surface fitting and sealing directly against the column tube wall.

23. A chromatography column according to claim 18 in which the outwardly-directed sealing portion includes a rubber sealing ring.

* * * * *

UNITED STATES PATENT AND TRADEMARK OFFICE
CERTIFICATE OF CORRECTION

PATENT NO.    : 6,811,688 B1
DATED         : November 2, 2004
INVENTOR(S)   : Martin John Hofmann It is certified that error appears in the above-identified patent and that said Letters Patent is hereby corrected as shown below:

Title page,
Item [86], PCT 371(c)(1), (2),(4) Date:, should be:
-- Feb.15, 2002 --.
Item [30], Foreign Application Priorty Data, should be:
-- May 20, 1999 (GB) ..................... 9911797 --.
Item [56], References Cited, OTHER PUBLICATIONS, delete "Iosoh Corp 129 Aug. 1991," and insert -- (Tosoh Corp.) 29 Aug. 1991, --.

Signed and Sealed this

Twenty-second Day of February, 2005

JON W. DUDAS
*Director of the United States Patent and Trademark Office*